(12) United States Patent
Michihata et al.

(10) Patent No.: US 10,893,186 B2
(45) Date of Patent: Jan. 12, 2021

(54) MEDICAL IMAGING APPARATUS AND MEDICAL OBSERVATION SYSTEM

(71) Applicant: Sony Olympus Medical Solutions Inc., Tokyo (JP)

(72) Inventors: Taihei Michihata, Kanagawa (JP); Takahiro Yamamoto, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/508,302

(22) Filed: Jul. 11, 2019

(65) Prior Publication Data
US 2020/0029010 A1 Jan. 23, 2020

(30) Foreign Application Priority Data
Jul. 18, 2018 (JP) .................................. 2018-135316

(51) Int. Cl.
*H04N 5/232* (2006.01)
*G02B 7/09* (2006.01)
*A61B 1/04* (2006.01)
*A61B 1/00* (2006.01)

(52) U.S. Cl.
CPC ..... *H04N 5/23212* (2013.01); *A61B 1/00167* (2013.01); *A61B 1/042* (2013.01); *G02B 7/09* (2013.01)

(58) Field of Classification Search
CPC ............ A61B 1/00006; A61B 1/00009; A61B 1/00105; A61B 1/00167; A61B 1/00188; A61B 1/042; A61B 1/07; G02B 7/09; H04N 2005/2255; H04N 5/2256; H04N 5/232; H04N 5/23212; H04N 5/232123; H04N 9/045; H04N 9/64
See application file for complete search history.

(56) References Cited

U.S. PATENT DOCUMENTS

| | | | |
|---|---|---|---|
| 2012/0120305 A1* | 5/2012 | Takahashi | H04N 5/23203 348/352 |
| 2013/0253313 A1* | 9/2013 | Kang | A61B 1/00165 600/425 |
| 2016/0000306 A1* | 1/2016 | Takayama | G02B 23/2484 600/109 |
| 2019/0179110 A1* | 6/2019 | Takinoiri | H04N 5/232123 |
| 2019/0374092 A1* | 12/2019 | Wu | G01J 3/0224 |

FOREIGN PATENT DOCUMENTS

JP 2013-081556 A 5/2013

\* cited by examiner

*Primary Examiner* — Mohammed S Rahaman
(74) *Attorney, Agent, or Firm* — Xsensus, LLP (57) ABSTRACT

A medical imaging apparatus includes: an image sensor configured to capture a subject image of a subject gathered by a fiberscope and emitted from proximal ends of optical fibers; a lens unit including a focus lens moving along an optical axis to adjust a focus, the lens unit being configured to form the subject image emitted from the proximal ends of the optical fibers on the image sensor; lens driving circuitry configured to move the focus lens along the optical axis; and a lens controller configured to perform, when the fiberscope is connected, a first auto-focus control of operating the lens driving circuitry to move the focus lens in a first movement range, evaluating a focusing state of the subject image, and positioning the focus lens at a position deviated from a first lens position at which the proximal ends of the optical fibers are focused.

13 Claims, 6 Drawing Sheets

MEDICAL IMAGING APPARATUS AND MEDICAL OBSERVATION SYSTEM

CROSS-REFERENCE TO RELATED APPLICATION

The present application claims priority to and incorporates by reference the entire contents of Japanese Patent Application No. 2018-135316 filed in Japan on Jul. 18, 2018.

BACKGROUND

The present disclosure relates to a medical imaging apparatus and a medical observation system.

In the related art, a medical imaging apparatus to which a fiberscope including a plurality of optical fibers is connected has been known (for example, see JP 2013-81556 A)

The medical imaging apparatus (an imaging device and an image data correction device) described in JP 2013-81556 A captures a subject image of a subject gathered by the fiberscope and emitted from proximal ends of the plurality of optical fibers.

Here, the optical fiber includes a core portion which transmits light and a clad portion provided on an outer circumferential surface of the core portion. The clad portion is a non-light transmitting portion which does not transmit light. Further, a gap between optical fibers in a configuration in which the optical fibers are bundled together also does not transmit light, and thus is a part of the non-light transmitting portion. As a result, since the non-light transmitting portion described above does not transmit light, a lattice pattern with low brightness corresponding to the non-light transmitting portion is present in the captured image captured by the medical imaging apparatus in some cases. Further, when the lattice pattern is present in the captured image, it is difficult to observe the subject.

Therefore, in the medical imaging apparatus described in JP 2013-81556 A, image processing is performed on the captured image to blur the lattice pattern present in the captured image.

SUMMARY

When the image processing is performed on the captured image to blur the lattice pattern present in the captured image, like the medical imaging apparatus described in JP 2013-81556 A, a false color is generated in the captured image due to the image processing. That is, the lattice pattern becomes less apparent, but the false color is generated. As a result, image quality of the captured image is degraded, which is problematic.

According to one aspect of the present disclosure, there is provided a medical imaging apparatus to which a fiberscope including a plurality of optical fibers is connectable, the medical imaging apparatus including: an image sensor configured to capture a subject image of a subject gathered by the fiberscope and emitted from proximal ends of the plurality of optical fibers; a lens unit including a focus lens moving along an optical axis to adjust a focus, the lens unit being configured to form the subject image emitted from the proximal ends of the plurality of optical fibers on the image sensor; lens driving circuitry configured to move the focus lens along the optical axis; and a lens controller configured to perform, when the fiberscope is connected to the medical imaging apparatus, a first auto-focus control of operating the lens driving circuitry to move the focus lens in a first movement range, evaluating a focusing state of the subject image, and positioning the focus lens at a position deviated from a first lens position at which the proximal ends of the optical fibers are focused.

DETAILED DESCRIPTION

Hereinafter, an embodiment for implementing the present disclosure (hereinafter, referred to as the embodiment) will be described with reference to the drawings. It should be noted that the present disclosure is not limited to the embodiment to be described below. Further, the same component is denoted by the same reference numeral in a description with reference to the drawings.

Configuration of Medical Observation System

Figure 1:
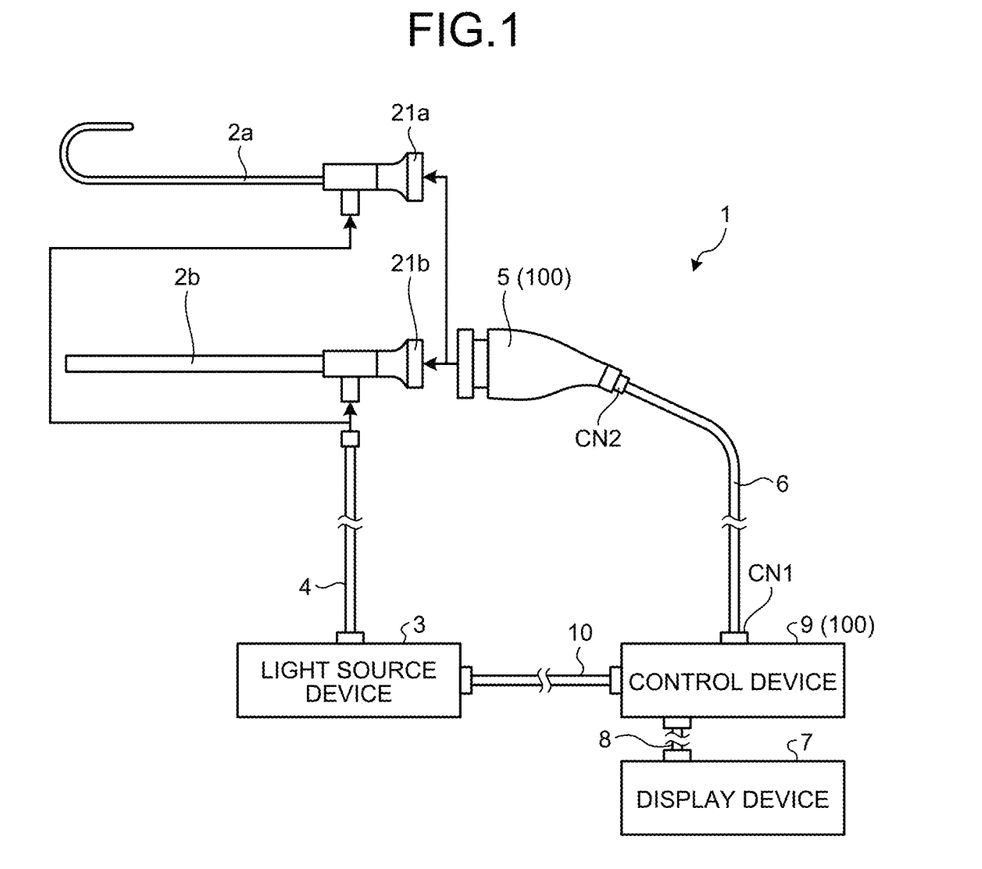
FIG. 1 is a view illustrating a configuration of a medical observation system according to an embodiment.

FIG. 1 is a view illustrating a configuration of a medical observation system 1 according to the present embodiment.

The medical observation system 1 is a system used in the medical field to observe the inside of a subject (the inside of a living body), and is configured so that an insertion unit which is inserted into the living body may be changed to a fiberscope 2a (FIG. 1) or a rigid endoscope 2b (FIG. 1) depending on an observation target or the like.

As illustrated in FIG. 1, the medical observation system 1 includes the fiberscope 2a, the rigid endoscope 2b, a light source device 3, a light guide 4, a camera head 5, a first transmission cable 6, a display device 7, a second transmission cable 8, a control device 9, and a third transmission cable 10.

The fiberscope 2a is formed by bundling a plurality of (hundreds to tens of thousands) flexible optical fibers (not illustrated) together, has a distal end provided with a lens (not illustrated) and a proximal end provided with a first eyepiece 21a (FIG. 1), and is inserted into the living body.

The rigid endoscope 2b has an elongated shape, which is entirely rigid or is partially flexible and partially rigid, has a proximal end provided with a second eyepiece 21b (FIG. 1), and is inserted into the living body. In the rigid endoscope 2b, an optical system which is constituted by one lens or a plurality of lenses and collects a subject image is provided.

In the present embodiment, first and second tags 22a and 22b (see FIG. 2) such as a radio frequency identification (RFID) tag or the like are provided at the first and second eyepieces 21a and 21b, respectively. Further, first identification information specific to the fiberscope 2a is recorded in the first tag 22a. Further, second identification information specific to the rigid endoscope 2b is recorded in the second tag 22b.

The light source device 3 is connected to one end of the light guide 4, and supplies light for lighting up the inside of the living body to an end of the light guide 4 according to a control by the control device 9. In the present embodiment, the light source device 3 is implemented separately from the control device 9. However, the present disclosure is not limited thereto and a configuration in which the light source device 3 is provided in the control device 9 may be adopted.

The light guide 4 has one end detachably connected to the light source device 3 and the other end detachably connected to the fiberscope 2a or the rigid endoscope 2b. Further, the light guide 4 transfers light supplied from the light source device 3 from one end to the other end to supply the light to the fiberscope 2a or the rigid endoscope 2b. The light supplied to the fiberscope 2a or the rigid endoscope 2b is emitted from a distal end of the fiberscope 2a or the rigid endoscope 2b and radiated to the inside of the living body. The light (subject image) radiated to the inside of the living body and reflected in the inside of the living body is gathered by the fiberscope 2a or the rigid endoscope 2b.

The camera head 5 is detachably connected to the first eyepiece 21a of the fiberscope 2a or the second eyepiece 21b of the rigid endoscope 2b. Further, the camera head 5 captures a subject image gathered by the fiberscope 2a or the rigid endoscope 2b and emitted from proximal ends of the plurality of optical fibers constituting the fiberscope 2a or the proximal end of the rigid endoscope 2b, and outputs an image signal (RAW signal) obtained by the capturing according to the control by the control device 9. The image signal is, for example, an image signal of 4K or more.

It should be noted that a detailed configuration of the camera head 5 will be described later.

The first transmission cable 6 has one end detachably connected to the control device 9 through a connector CN1 (FIG. 1) and the other end detachably connected to the camera head 5 through a connector CN2 (FIG. 1). Further, the first transmission cable 6 transmits the image signal or the like output from the camera head 5 to the control device 9, and transmits a control signal, a synchronization signal, clock, power, and the like, each of which is output from the control device 9, to the camera head 5.

It should be noted that in the transmission of the image signal and the like from the camera head 5 to the control device 9 through the first transmission cable 6, the image signal and the like may be transmitted in a form of an optical signal, or may be transmitted in a form of an electric signal. The same applies to the transmission of the control signal, the synchronization signal, and the clock from the control device 9 to the camera head 5 through the first transmission cable 6.

The display device 7 is implemented by a display using a liquid crystal, organic electro luminescence (EL), and the like, and displays an image based on a video signal from the control device 9 according to the control by the control device 9.

The second transmission cable 8 has one end detachably connected to the display device 7 and the other end detachably connected to the control device 9. Further, the second transmission cable 8 transmits the video signal processed by the control device 9 to the display device 7.

The control device 9 includes a central processing unit (CPU) and the like, and collectively controls operations of the light source device 3, the camera head 5, and the display device 7.

It should be noted that a detailed configuration of the control device 9 will be described later.

The third transmission cable 10 has one end detachably connected to the light source device 3 and the other end detachably connected to the control device 9. Further, the third transmission cable 10 transmits the control signal from the control device 9 to the light source device 3.

Configuration of Camera Head

Next, a configuration of the camera head 5 will be described.

Figure 2:
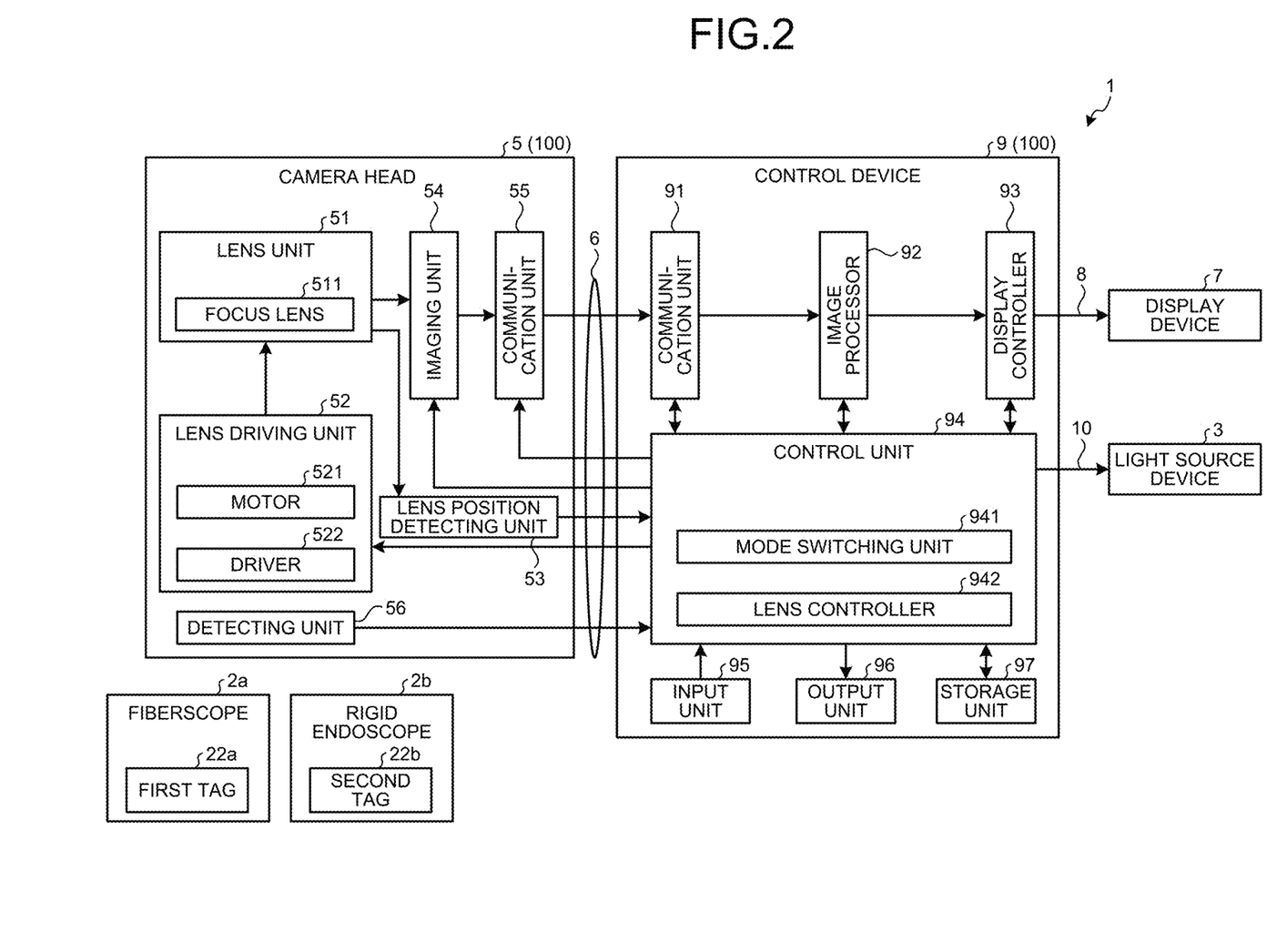
FIG. 2 is a block diagram illustrating a configuration of a camera head and a control device.

FIG. 2 is a block diagram illustrating a configuration of the camera head 5 and the control device 9.

For convenience of explanation, the connectors CN1 and CN2 between the control device 9 and the camera head 5, and the first transmission cable 6, connectors between the control device 9 and the display device 7, and the second transmission cable 8, and connectors between the control device 9 and the light source device 3, and the third transmission cable 10 are omitted in FIG. 2.

As illustrated in FIG. 2, the camera head 5 includes a lens unit 51, a lens driving unit 52, a lens position detecting unit 53, an imaging unit 54, a communication unit 55, and a detecting unit 56.

The lens unit 51 forms the subject image gathered by the fiberscope 2a or the rigid endoscope 2b on an imaging surface of the imaging unit 54. As illustrated in FIG. 2, the lens unit 51 includes a focus lens 511.

The focus lens 511 is constituted by one lens or a plurality of lenses and moves along an optical axis to adjust the focus.

Further, a focus mechanism (not illustrated) which moves the focus lens 511 along the optical axis is provided in the lens unit 51.

As illustrated in FIG. 2, the lens driving unit 52 includes a motor 521 which operates the focus mechanism described above and a driver 522 which drives the motor 521. Further, the lens driving unit 52 adjusts the focus of the lens unit 51 according to the control by the control device 9.

The lens position detecting unit 53 is constituted by a position sensor such as a photo interrupter or the like, and detects a lens position (hereinafter, referred to as a focus position) of the focus lens 511. Further, the lens position detecting unit 53 outputs a detection signal according to the focus position to the control device 9 through the first transmission cable 6.

The imaging unit 54 captures the subject image according to the control by the control device 9. Although not specifically illustrated, the imaging unit 54 includes an image sensor, such as a charge coupled device (CCD), a complementary metal oxide semiconductor (CMOS), or the like, which receives the subject image formed by the lens unit 51 and converts the subject image into an electric signal (analog signal), and a signal processor which performs signal processing on the electric signal (analog signal) from the image sensor to output an image signal (RAW signal (digital signal)).

The communication unit 55 functions as a transmitter that transmits the image signal (RAW signal (digital signal)) output from the imaging unit 54 to the control device 9 through the first transmission cable 6. The communication unit 55 is implemented by, for example, a high-speed serial interface that performs, with the control device 9 through the first transmission cable 6, communication of the image signal at a transmission rate of 1 Gbps or more.

The detecting unit 56 is constituted by, for example, an RFID detection circuit or the like, and acquires the first identification information recorded in the first tag 22a or the second identification information recorded in the second tag 22b according to the control by the control device 9. Further, the detecting unit 56 outputs the acquired first identification information or the acquired second identification information to the control device 9 through the first transmission cable 6.

Configuration of Control Device

Next, a configuration of the control device 9 will be described with reference to FIG. 2.

As illustrated in FIG. 2, the control device 9 includes a communication unit 91, an image processor 92, a display controller 93, a control unit 94, an input unit 95, an output unit 96, and a storage unit 97.

The communication unit 91 functions as a receiver that receives the image signal (RAW signal (digital signal)) output from the camera head 5 (communication unit 55) through the first transmission cable 6. The communication unit 91 is implemented for example, a high-speed serial interface that performs, with the communication unit 55, communication of the image signal at a transmission rate of 1 Gbps or more.

The image processor 92 processes the image signal (RAW signal (digital signal)) output from the camera head 5 (communication unit 55) and received by the communication unit 91 according to the control by the control unit 94.

For example, the image processor 92 multiplies the image signal (RAW signal (digital signal)) by a digital gain amplifying the digital signal. Further, the image processor 92 performs RAW processing such as an optical black subtraction process, a demosaicing process, or the like on the image signal (RAW signal (digital signal)) after the multiplication by the digital gain, and converts the RAW signal (image signal) into an RGB signal (image signal). In addition, the image processor 92 converts the RGB signal (image signal) into a luminance signal and a chrominance signal (Y, $C_B/C_R$ signal). Further, the image processor 92 performs, on the image signal (digital signal), a correction process such as a white balance adjustment process, gamma correction, contour enhancement, color tone correction, or the like. In addition, the image processor 92 performs, on the image signal (Y, $C_B/C_R$ signal or the like), a detection process for controlling (performing first and second auto-focus controls) the camera head 5, which will be described later.

For example, the image processor 92 detects a contrast or a frequency component of an image in a detection area, which is a partial area of the entire captured image of one frame captured by the imaging unit 54, based on pixel information (luminance signal (Y signal) or the like) of each pixel of the detection area. Further, the image processor 92 outputs, to the control unit 94, detection information (the contrast, the frequency component, or the like) obtained by the detection.

The display controller 93 generates a video signal for display based on the image signal (Y, $C_B/C_R$ signal) processed by the image processor 92 according to the control by the control unit 94. Further, the display controller 93 outputs the video signal to the display device 7 through the second transmission cable 8. By doing so, the display device 7 displays the captured image based on the video signal.

The control unit 94 is implemented by, for example, a CPU or the like, and outputs a control signal through the first to third transmission cables 6, 8, and 10, thereby controlling an entire operation of the control device 9 in addition to controlling operations of the light source device 3, the camera head 5, and the display device 7. As illustrated in FIG. 2, the control unit 94 includes a mode switching unit 941 and a lens controller 942.

The mode switching unit 941 compares the first identification information or the second identification information acquired by the detecting unit 56 with reference information stored in the storage unit 97 and determines whether or not the fiberscope 2a is connected to the camera head 5, or whether or not the rigid endoscope 2b is connected to the camera head 5. Further, the mode switching unit 941 switches a mode of the lens controller 942 to a fiber mode when it is determined that the fiberscope 2a is connected to the camera head 5. Meanwhile, the mode switching unit 941 switches the mode of the lens controller 942 to a normal mode when it is determined that the rigid endoscope 2b is connected to the camera head 5.

The lens controller 942 performs the first auto-focus control when the mode of the lens controller 942 is switched to the fiber mode by the mode switching unit 941. Meanwhile, the lens controller 942 performs the second auto-focus control when the mode of the lens controller 942 is switched to the normal mode by the mode switching unit 941.

It should be noted that a detailed description of the first and second auto-focus controls will be provided later.

The input unit 95 is implemented by an operation device such as a mouse, a keyboard, a touch panel, or the like, and receives a user operation by a user such as a doctor or the like. Further, the input unit 95 outputs, to the control unit 94, an operation signal according to the user operation.

The output unit 96 is implemented by a speaker, a printer, or the like and outputs various kinds of information.

The storage unit 97 stores a program executed by the control unit 94, information for the processing performed by the control unit 94, or the like. As the information for the processing performed by the control unit 94, the reference information used by the mode switching unit 941 and first and second movement range information used by the lens controller 942 may be illustrated.

The reference information is information including first association information in which first scope information indicating the fiberscope is associated with the first identification information, and second association information in which second scope information indicating the rigid endoscope is associated with the second identification information. In other words, when the first identification information is acquired by the detecting unit 56, the mode switching unit 941 recognizes that the first scope information is associated with the first identification information as a result of comparing the first identification information with the reference information, thereby determining that the fiberscope 2a is connected to the camera head 5. Meanwhile, when the second identification information is acquired by the detecting unit 56, the mode switching unit 941 recognizes that the second scope information is associated with the second identification information as a result of comparing the second identification information with the reference information, thereby determining that the rigid endoscope 2b is connected to the camera head 5.

A detailed description of the first and second movement range information will be provided later.

The camera head 5 and the control device 9 described above correspond to a medical imaging apparatus 100 (FIGS. 1 and 2) according to the present disclosure.

Operation of Control Device

Next, an operation of the control device 9 described above will be described.

Figure 3:
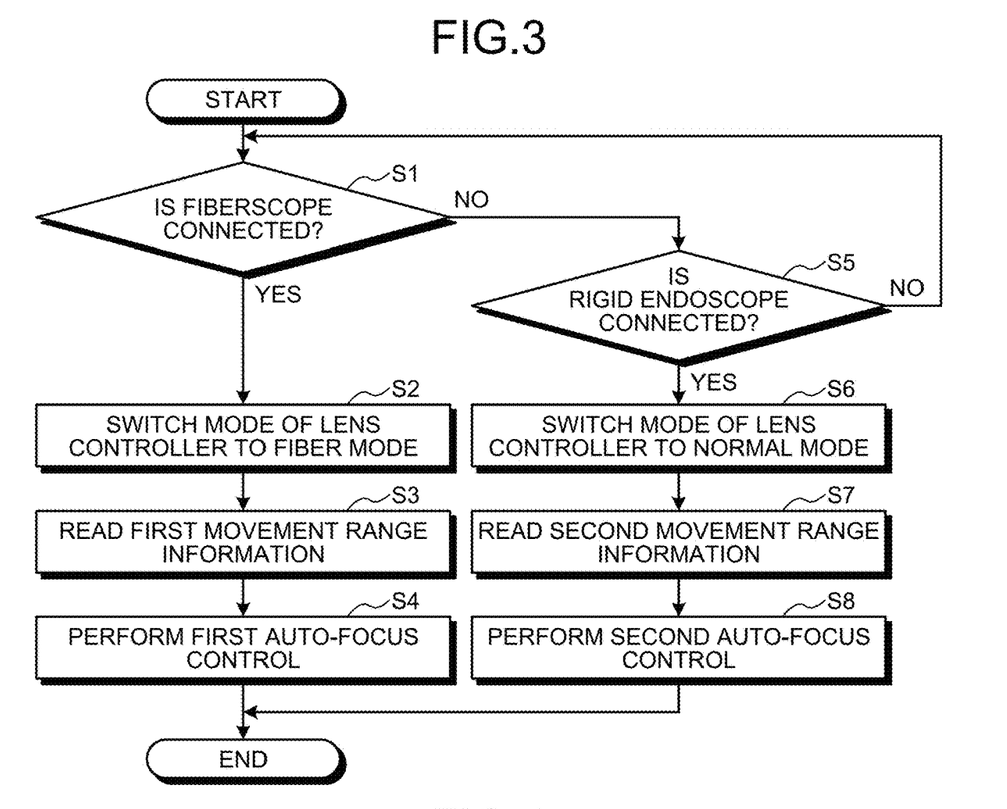
FIG. 3 is a flowchart illustrating an operation of the control device.

FIG. 3 is a flowchart illustrating an operation of the control device 9.

Hereinafter, for convenience of explanation, the first and second auto-focus controls will be mainly described as the operation of the control device 9.

First, the mode switching unit 941 outputs a control signal to the detecting unit 56 through the first transmission cable 6 so that the detecting unit 56 acquires the first identification information stored in the first tag 22a or the second identification information stored in the second tag 22b. Further, the mode switching unit 941 compares the first identification information or the second identification information acquired by the detecting unit 56 with the reference information stored in the storage unit 97 and determines whether or not the fiberscope 2a is connected to the camera head 5 (Step S1).

When it is determined that the fiberscope 2a is connected to the camera head 5 (Step S1: Yes), the mode switching unit 941 switches the mode of the lens controller 942 to the fiber mode (Step S2).

After Step S2, the lens controller 942 reads the first movement range information from the storage unit 97 (Step S3), and performs the first auto-focus control to be described later (Step S4). Thereafter, the control device 9 ends the present control flow.

Figure 4:
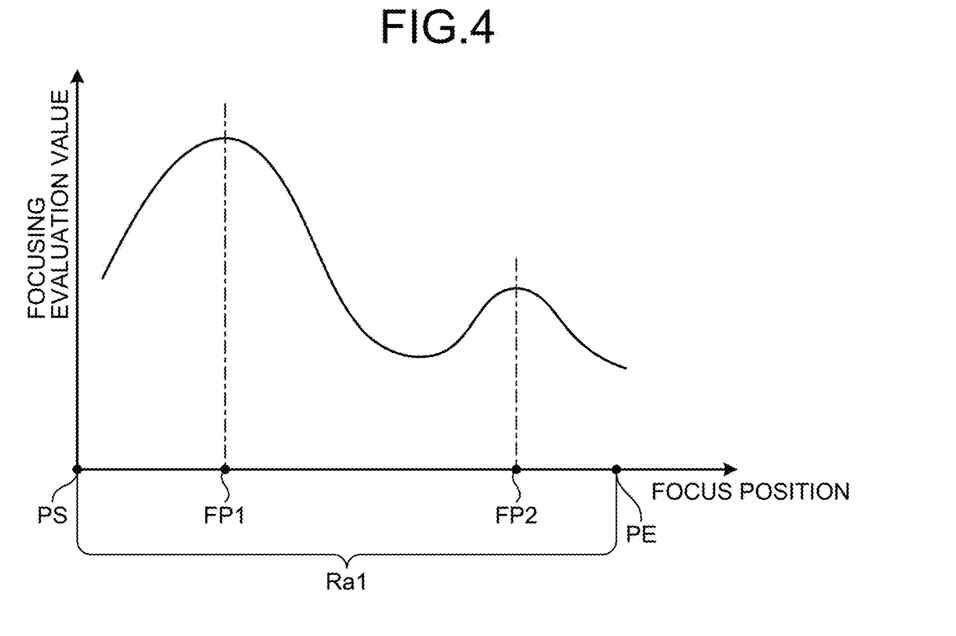
FIG. 4 is a view for describing a first auto-focus control.

FIG. 4 is a view for describing the first auto-focus control. Specifically, in FIG. 4, a horizontal axis represents a focus position. In FIG. 4, the left side indicates a focus position adjacent to a proximal point and the right side indicates a focus position adjacent to a distal point (subject). Further, a vertical axis represents a focusing evaluation value for evaluating a focusing state of the subject image. Further, FIG. 4 illustrates a behavior of the focusing evaluation value in a case of changing the focus position.

Here, the first movement range information is information indicating a first movement range Ra1 (FIG. 4) in which the focus position is changed (the focus lens 511 is moved) in the first auto-focus control. In detail, the first movement range Ra1 is a range from a focus position PS (hereinafter, referred to as a movement start position PS) at which an object present between the proximal ends of the optical fibers constituting the fiberscope 2a and the focus lens 511 is focused to a focus position PE (hereinafter, referred to as a movement end position PE) at which an object present at a position located at a distance of about 10 cm to 20 cm from the distal end of the fiberscope 2a toward the subject is focused.

In detail, in Step S4, the lens controller 942 operates the lens driving unit 52 to change a position of the focus lens 511 from the movement start position PS to the movement end position PH and sequentially calculates the focusing evaluation value, and controls the storage unit 97 to sequentially store first focus information in which the focus position detected by the lens position detecting unit 53 is associated with the focusing evaluation value corresponding to the focus position.

Here, as the focusing evaluation value, a contrast detected by the image processor 92 and a sum of high-frequency components among frequency components detected by the image processor 92 may be illustrated. It should be noted that the larger the focusing evaluation value, the better the focusing.

Further, the lens controller 942 calculates a peak position (focus position FP2 (FIG. 4)) at which the focusing evaluation value becomes second-largest based on a plurality of pieces of first focus information stored in the storage unit 97. Further, the lens controller 942 calculates, based on the focus position FP2 and a current focus position detected by the lens position detecting unit 53, a movement direction (a direction toward the proximal point or a direction toward the distal point) and a movement amount, in which the focus lens 511 is to be moved from the current focus position to the focus position FP2. Further, the lens controller 942 outputs, to the lens driving unit 52, a control signal according to the movement direction and the movement amount, and positions the focus lens 511 at the focus position FP2. As described above, in the present embodiment, the lens controller 942 performs the first auto-focus control by using a so-called hill-climbing method.

Figure 5:
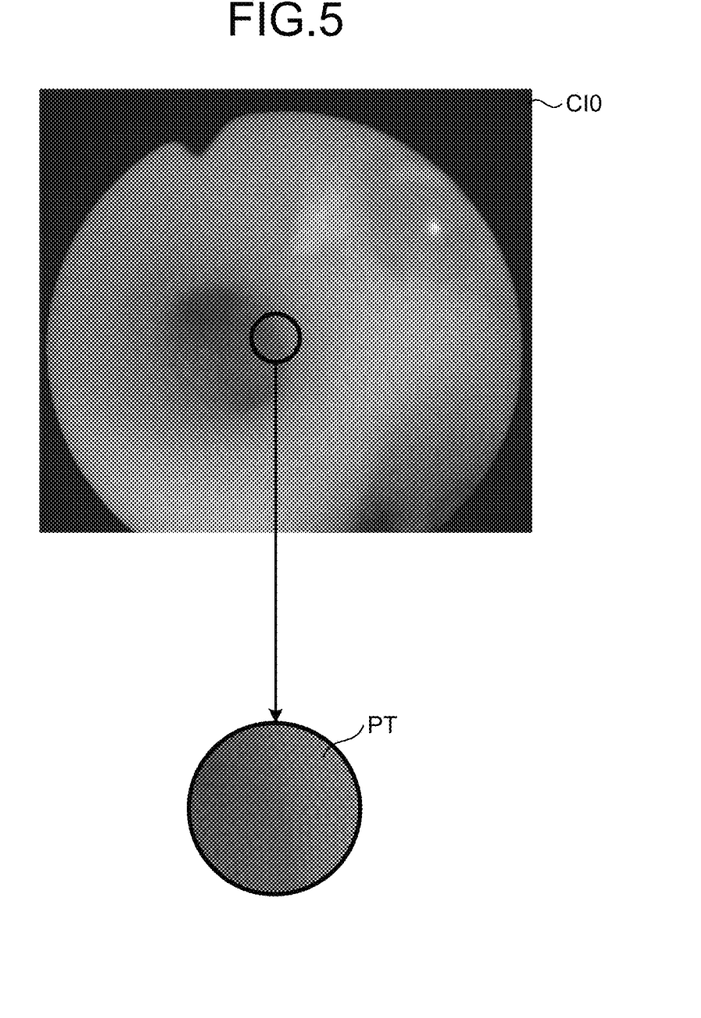
FIG. 5 is a view for describing a captured image generated by performing the first auto-focus control.
Figure 6:
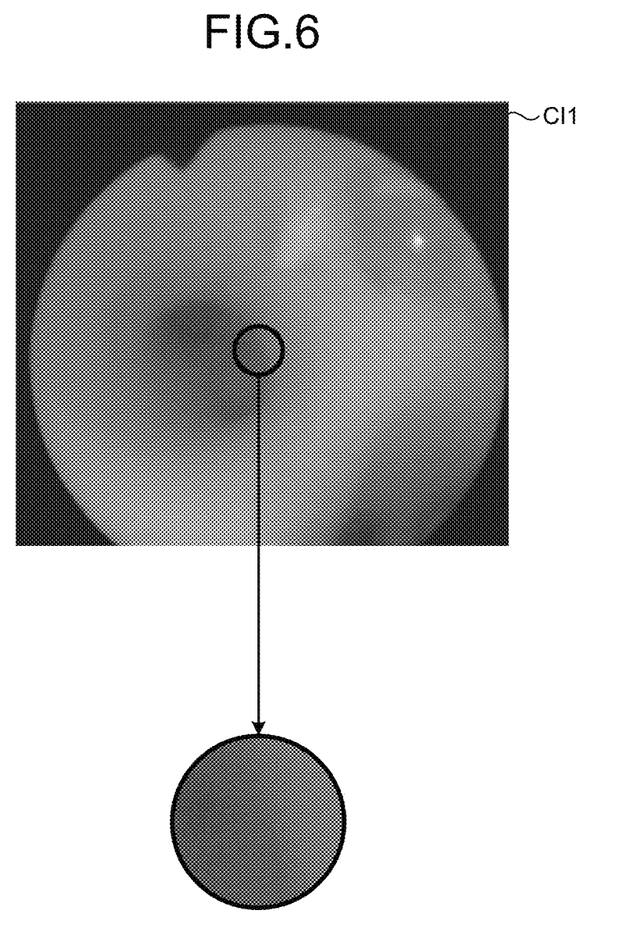
FIG. 6 is a view for describing a captured image generated by performing the first auto-focus control.

FIGS. 5 and 6 are views for describing a captured image CI1 generated by performing the first auto-focus control. In detail, FIG. 5 is a view illustrating a captured image CI0 generated in a case of positioning the focus lens 511 at a peak position (focus position FP1) at which the focusing evaluation value becomes largest, in the first auto-focus control. FIG. 6 is a view illustrating a captured image CI1 generated in a case of positioning the focus lens 511 at the focus position FP2, in the first auto-focus control.

Here, the focus position FP1, which is located closer to the proximal point than the focus position FP2 is, is a focus position at which the proximal ends of the plurality of optical fibers constituting the fiberscope 2a are focused, and corresponds to a first lens position according to the present disclosure. For this reason, in a case of positioning the focus lens 511 at the focus position FP1, as illustrated in FIG. 5, a lattice pattern PT with low brightness corresponding to the non-light transmitting portion (the clad portion, the gap between the optical fibers, and the like) in the plurality of optical fibers is present in the captured image CI0.

Meanwhile, the focus position FP2 is a focus position at which the subject is focused, and corresponds to a second lens position according to the present disclosure. For this reason, in a case of positioning the focus lens 511 at the focus position FP2, as illustrated in FIG. 6, the lattice pattern PT described above is not present and the captured image CI1 becomes an image in which the subject is clear.

Returning to Step S1, when it is determined that the fiberscope 2a is not connected to the camera head 5 (Step S1: No), the mode switching unit 941 compares the first identification information or the second identification information acquired by the detecting unit 56 with the reference information stored in the storage unit 97 and determines whether or not the rigid endoscope 2b is connected to the camera head 5 (Step S5).

When it is determined that the rigid endoscope 2b is not connected to the camera head 5 (Step S5: No), the control device 9 returns to Step S1.

Meanwhile, when it is determined that the rigid endoscope 2b is connected to the camera head 5 (Step S5: Yes), the mode switching unit 941 switches the mode of the lens controller 942 to the normal mode (Step S6).

After Step S6, the lens controller 942 reads the second movement range information from the storage unit 97 (Step S7), and performs the second auto-focus control to be described later (Step S8). Thereafter, the control device 9 ends the present control flow.

Figure 7:
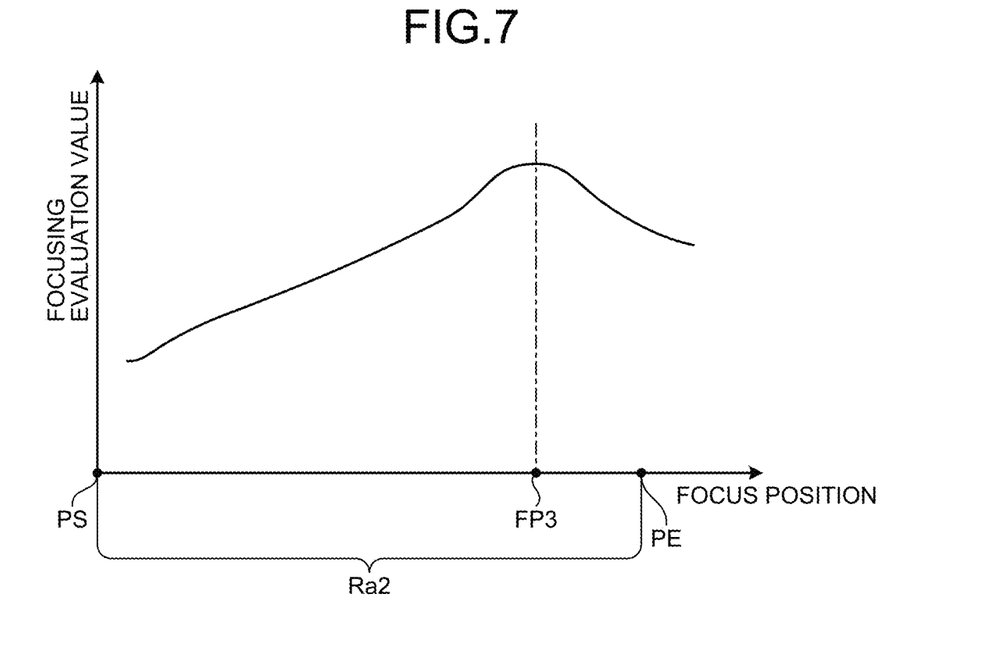
FIG. 7 is a view for describing a second auto-focus control.

FIG. 7 is a view for describing the second auto-focus control. Specifically, FIG. 7 corresponds to FIG. 4.

Here, the second movement range information is information indicating a second movement range Ra2 (FIG. 7) in which the focus position is changed in the second auto-focus control. In the present embodiment, the second movement range Ra2 is the same range as the first movement range Ra2. That is, the second movement range Ra2 is a range from the movement start position PS to the movement end position PE.

In detail, in Step S8, the lens controller 942 operates the lens driving unit 52 to change a position of the focus lens 511 from the movement start position PS to the movement end position PE and sequentially calculates the focusing evaluation value, and controls the storage unit 97 to sequentially store second focus information in which the focus position detected by the lens position detecting unit 53 is associated with the focusing evaluation value corresponding to the focus position.

Further, the lens controller 942 calculates a peak position (focus position FP3 (FIG. 7)) at which the focusing evaluation value becomes largest based on a plurality of pieces of second focus information stored in the storage unit 97. Further, the lens controller 942 calculates, based on the focus position FP3 and a current focus position detected by the lens position detecting unit 53, a movement direction (a direction toward the proximal point or a direction toward the distal point) and a movement amount, in which the focus lens 511 is to be moved from the current focus position to the focus position FP3. Further, the lens controller 942 outputs, to the lens driving unit 52, a control signal according to the movement direction and the movement amount, and positions the focus lens 511 at the focus position FP3. As described above, in the present embodiment, the lens controller 942 performs the second auto-focus control by using the so-called hill-climbing method, similarly to the first auto-focus control.

Here, the focus position FP3 is a focus position at which the subject is focused, and corresponds to the second lens position according to the present disclosure. For this reason, in a case of positioning the focus lens 511 at the focus position FP3, a captured image (not illustrated) becomes an image in which the subject is clear.

The first and second auto-focus controls described above may adopt a so-called continuous auto-focus (AF) which is performed all the time, or may adopt a so-called one-touch AF which is performed depending on an operation of an operation button (not illustrated) provided in the camera head 5 or the like.

According to the present embodiment described above, the following effects are exhibited.

The medical imaging apparatus 100 according to the present embodiment performs the first auto-focus control when the fiberscope 2a is connected to the medical imaging apparatus 100. That is, the medical imaging apparatus 100 operates the lens driving unit 52 to move the focus lens 511 in the first movement range Ra1 and evaluates a focusing state of the subject image. Further, the medical imaging apparatus 100 positions the focus lens 511 at the focus position FP2 deviated from the focus position FP1 at which the proximal ends of the optical fibers constituting the fiberscope 2a are focused.

For this reason, the captured image CI1 becomes an image in which the lattice pattern PT caused by the plurality of optical fibers constituting the fiberscope 2a is less apparent. Further, the lattice pattern PT is made less apparent by changing the focus position rather than performing image processing, and thus a false color caused by the image processing is not generated in the captured image CI1.

Therefore, by the medical imaging apparatus 100 according to the present embodiment, it is possible to make the lattice pattern PT caused by the plurality of optical fibers less apparent and generate the captured image CI1 of which image quality degradation caused by a false color is suppressed.

In particular, the focus position FP2 is a position deviated from the focus position FP1 toward the distal point. Therefore, in the captured image CI1, the subject is not, blurred as compared to the case where the focus position FP2 is a position deviated from the focus position FP1 toward the proximal point.

In addition, the focus position FP2 is a focus position at which the subject is focused. For this reason, the captured image CI1 in which the subject is clear may be generated.

The focus position FP2 at which the subject is focused is located relatively adjacent to the proximal point.

Further, the medical imaging apparatus 100 according to the present embodiment moves the focus lens 511 from a proximal point side toward a distal point side in the first movement range Ra1 in the first auto-focus control. For this reason, it is possible to rapidly find the focus position FP2 in the first auto-focus control. That is, it is possible to rapidly perform the first auto-focus control.

Further, the rigid endoscope 2b may also be connected to the medical imaging apparatus 100 according to the present embodiment. Further, the medical imaging apparatus 100 performs the second auto-focus control when the rigid endoscope 2b is connected to the medical imaging apparatus 100. That is, the medical imaging apparatus 100 operates the lens driving unit 52 to move the focus lens 511 in the second movement range Ra2, evaluates a focusing state of the subject image, and positions the focus lens 511 at the focus position FP3 at which the subject is focused.

For this reason, in both of the case where the fiberscope 2a is connected to the medical imaging apparatus 100 and the case where the rigid endoscope 2b is connected to the medical imaging apparatus 100, it is possible to generate a captured image in which the subject is clear and improve convenience.

Modified Example of Embodiment

Figure 8:
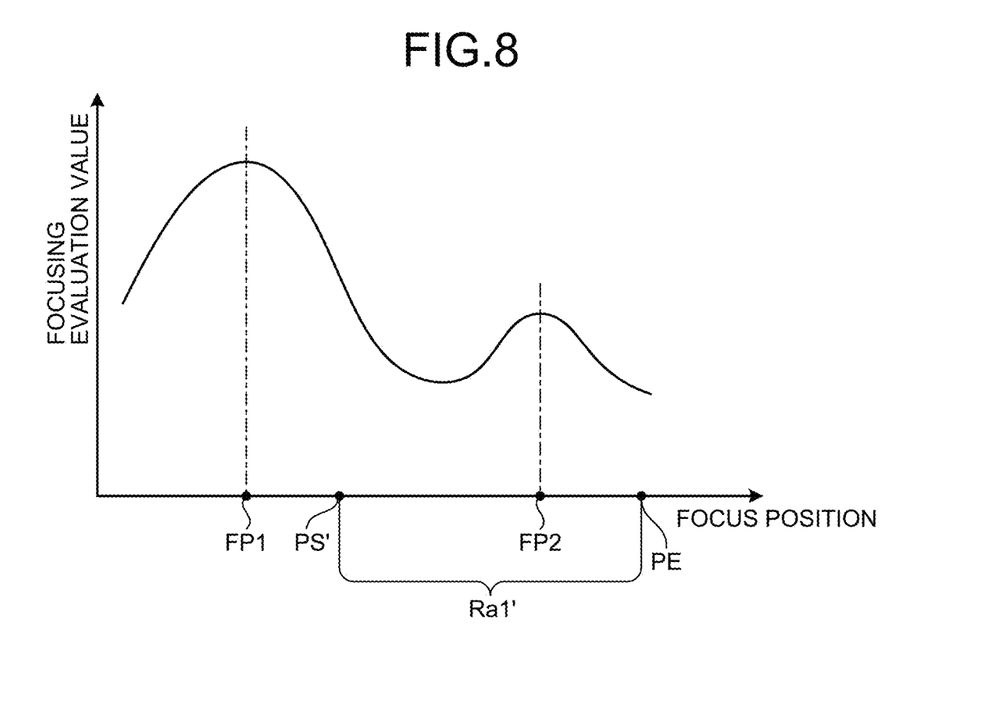
FIG. 8 is a view illustrating a modified example of the embodiment.

FIG. 8 is a view illustrating a modified example of the present embodiment. Specifically, FIG. 8 corresponds to FIG. 4.

In the embodiment described above, as the first movement range information, information indicating a first movement range Ra1' according to the present modified example illustrated in FIG. 8 may be adopted. In detail, the first movement range Ra1' is a range from a movement start position PS', which is located closer to the distal point than the focus position FP1 is, to the movement end position PE.

Further, when the information indicating the first movement range Ra1' is adopted as the first movement range information, the lens controller 942 performs the first auto-focus control to be described below in Step S4.

In detail, in Step S4, the lens controller 942 operates the lens driving unit 52 to change a position of the focus lens 511 from the movement start position PS' to the movement end position PE and sequentially calculates the focusing evaluation value, and controls the storage unit 97 to sequentially store first focus information in which the focus position detected by the lens position detecting unit 53 is associated with the focusing evaluation value corresponding to the focus position.

Further, the lens controller 942 calculates a peak position (focus position FP2 (FIG. 8)) at which the focusing evaluation value becomes largest based on a plurality of pieces of second focus information stored in the storage unit 97. Further, the lens controller 942 calculates, based on the focus position FP2 and a current focus position detected by the lens position detecting unit 5, a movement direction (a direction toward the proximal point or a direction toward the distal point) and a movement amount, in which the focus lens 511 is to be moved from the current focus position to the focus position FP2. Further, the lens controller 942 outputs, to the lens driving unit 52, a control signal according to the movement direction and the movement amount, and positions the focus lens 511 at the focus position FP2.

Even when the first movement range Ra1' is adopted as in the present modified example described above, the same effects as those of the embodiment described above are exhibited.

Other Embodiments

Hereinabove, the embodiment of the present disclosure has been described, but the present disclosure is not limited to the embodiment described above and the modified example thereof.

In the embodiment described above and the modified example thereof, the focus position FP2 is not limited to the position described in the embodiment described above and the modified example thereof, but may be any other position as long as it is a position deviated from the focus position FP1.

In the embodiment described above and the modified example thereof, the focus lens 511 is moved from the proximal point side toward the distal point side in the first and second auto-focus controls. However, the present disclosure is not limited thereto, and the focus lens 511 may also be moved from the distal point side toward the proximal point side.

In the embodiment described above and the modified example thereof, whether the fiberscope 2a or the rigid endoscope 2b is connected to the camera head 5 is automatically determined by using the configuration including the first and second tags 22a and 22b, and the detecting unit 56, but the present disclosure is not limited thereto. For example, the operation button may be provided in the camera head 5 or the like, and the medical imaging apparatus 100 may recognize that the fiberscope 2a is connected to the camera head 5 or the rigid endoscope 2b is connected to the camera head 5, according to an operation on the operation button.

In the embodiment described above and the modified example thereof, some components of the camera head 5 or some components of the control device 9 may also be provided in, for example, the connector CN1 or CN2.

By the medical imaging apparatus and the medical observation system according to the present disclosure, it is possible to make a lattice pattern caused by a plurality of optical fibers less apparent and generate a captured image of which image quality degradation caused by a false color is suppressed.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging apparatus to which a fiberscope including a plurality of optical fibers is connectable, the medical imaging apparatus comprising:
   an image sensor to capture a subject image of a subject gathered by the fiberscope and emitted from proximal ends of the plurality of optical fibers;
   a focus lens to form the subject image emitted from the proximal ends of the plurality of optical fibers on the image sensor;
   circuitry configured to
   move the focus lens along the optical axis;
   perform, when the fiberscope is connected to the medical imaging apparatus, a first auto-focus control to move the focus lens in a first movement range towards a distal end, evaluate a focusing state of the subject image, and position the focus lens at a second lens position deviated from a first lens position at which the proximal ends of the optical fibers are focused, the first movement range including a third lens position at a local minimum focus evaluating value, wherein the second lens position is at a local maximum focus evaluating value after the third lens position towards the distal end, wherein the first lens position has a higher focusing evaluation value than the second lens position; and
   position the focus lens at the second lens position during image capture.

2. The medical imaging apparatus according to claim 1, wherein
   the first movement range is a range including the first lens position, and
   the circuitry is configured to move the focus lens from a proximal end toward the distal end in the first movement range, evaluate the focusing state of the subject image, and position the focus lens at a position at which the focus lens is further from the first lens position toward the distal end in the first auto-focus control.

3. The medical imaging apparatus according to claim 1, wherein
   the first movement range is a range starts closer to the distal end than the first lens position, and
   the circuitry is configured to move the focus lens away from a proximal end toward a distal end in the first movement range, evaluate the focusing state of the subject image, and position the focus lens at a position further from the first lens position toward the distal end in the first auto-focus control.

4. The medical imaging apparatus according to claim 1, wherein
   a rigid endoscope is connectable to the medical imaging apparatus,
   the image sensor captures the subject image gathered by the rigid endoscope and emitted from a proximal end of the rigid endoscope, and
   when the rigid endoscope is connected to the medical imaging apparatus, the circuitry is configured to perform a second auto-focus control to move the focus lens in a second movement range, evaluate the focusing state of the subject image, and position the focus lens at a fourth lens position at which the subject is focused.

5. The medical imaging apparatus according to claim 4, further comprising:
   a memory configured to store, respectively, first movement range information indicating the first movement range, and second movement range information indicating the second movement range,
   wherein when the fiberscope is connected to the medical imaging apparatus, the circuitry is configured to read the first movement range information from the memory and perform the first auto-focusing control to move the focus lens in the first movement range based on the first movement range information, evaluate the focusing state of the subject image, and position the focus lens at the second lens position, and
   when the rigid endoscope is connected to the medical imaging apparatus, the circuitry is configured to read the second movement range information from the memory and perform the second auto-focusing control to move the focus lens in the second movement range based on the second movement range information, evaluate the focusing state of the subject image, and position the focus lens at the fourth lens position.

6. A medical observation system comprising:
a fiberscope including a plurality of optical fibers; and
the medical imaging apparatus according to claim 1 to which the fiberscope is connectable.

7. The medical imaging apparatus according to claim 1, wherein the first movement range starts closer to the distal end than the first lens position.

8. The medical imaging apparatus according to claim 7, wherein the second lens position has a highest focusing evaluation value over the first movement range.

9. The medical imaging apparatus according to claim 7, wherein the second lens position is a first local maximum after the third lens position.

10. The medical imaging apparatus according to claim 1, wherein the second lens position has a second highest focusing evaluation value over the first movement range.

11. The medical imaging apparatus according to claim 1, wherein the focus lens is moved through the first movement range before evaluating the focus state.

12. The medical imaging apparatus according to claim 1, wherein the second lens position is a first local maximum after the third lens position.

13. The medical imaging apparatus according to claim 1, wherein the second lens position has a largest focus evaluating value after the third lens position towards the distal end.

* * * * *